US011759267B2

(12) United States Patent
Nahum et al.

(10) Patent No.: US 11,759,267 B2
(45) Date of Patent: Sep. 19, 2023

(54) AUTOMATIC REGISTRATION OF A ROBOT ARM FOR A MEDICAL INTERVENTION

(71) Applicant: Quantum Surgical, Montpellier (FR)

(72) Inventors: Bertin Nahum, Castelnau-le-Lez (FR); Fernand Badano, Lyons (FR); Lucien Blondel, Montpellier (FR); Frédéric Banegas, Jacou (FR); Sébastien Olive, Montpellier (FR)

(73) Assignee: QUANTUM SURGICAL, Montpellier (FR)

( * ) Notice: Subject to any disclaimer, the term of this patent is extended or adjusted under 35 U.S.C. 154(b) by 274 days.

(21) Appl. No.: 17/413,510

(22) PCT Filed: Dec. 11, 2019

(86) PCT No.: PCT/FR2019/053012
§ 371 (c)(1),
(2) Date: Jun. 11, 2021

(87) PCT Pub. No.: WO2020/120901
PCT Pub. Date: Jun. 18, 2020

(65) Prior Publication Data
US 2022/0061928 A1 Mar. 3, 2022

(30) Foreign Application Priority Data
Dec. 12, 2018 (FR) ...................... 1872735

(51) Int. Cl.
*A61B 34/20* (2016.01)
*A61B 34/10* (2016.01)
(Continued)

(52) U.S. Cl.
CPC ............. *A61B 34/20* (2016.02); *A61B 34/10* (2016.02); *A61B 34/30* (2016.02); *A61B 90/50* (2016.02);
(Continued)

(58) Field of Classification Search
CPC ......... A61B 34/10; A61B 34/20; A61B 34/30; A61B 2034/2051; A61B 90/50
See application file for complete search history.

(56) References Cited

U.S. PATENT DOCUMENTS

2016/0258782 A1  9/2016  Sadjadi et al.
2017/0202629 A1  7/2017  Maillet et al.

FOREIGN PATENT DOCUMENTS

WO     2018/167246 A1    9/2018

OTHER PUBLICATIONS

Nixon, Mark et al., "The Effects of Metals and Interfering Fields on Electromagnetic Trackers," Presence, vol. 7, No. 2, Apr. 1998, pp. 204-218.
(Continued)

*Primary Examiner* — Boniface Ngathi N
(74) *Attorney, Agent, or Firm* — ARENTFOX SCHIFF LLP (57) ABSTRACT

The invention relates to a method for positioning an articulated arm of a medical robot assisted by a navigation system comprising an electromagnetic field generator and two sensors. The generated field forms a measurement zone in which the position of a sensor can be determined by the navigation system and communicated to the robot. A first sensor is positioned at an anatomical location of interest of a patient. A second sensor is positioned on the articulated arm. When the two sensors are located in the measurement zone, a so-called "region of reduced influence" of the measurement zone is determined, in which the introduction of a metal object has virtually no influence on the determination of the position of the sensors by the navigation system. The articulated arm is then configured so that any metal part of the articulated arm located in the measurement zone is situated within the region of reduced influence.

14 Claims, 6 Drawing Sheets

(51) Int. Cl.
*A61B 34/30* (2016.01)
*A61B 90/50* (2016.01)
(52) U.S. Cl.
CPC . *A61B 2034/107* (2016.02); *A61B 2034/2051* (2016.02)

(56) References Cited

OTHER PUBLICATIONS

Much, Jilian, "Error Classification and Propagation for Electromagnetic Tracking," Technical University of Munich, Jan. 14, 2008, 102 pages.
International Search Report and Written Opinion for PCT/FR2019/053012, dated Mar. 23, 2020, 4 pages.
Hummel Johann et al., "Evaluation of a miniature electromagnetic position tracker," Medical Physics, AIP, vol. 29, No. 10, Oct. 1, 2002, pp. 2205-2212.

AUTOMATIC REGISTRATION OF A ROBOT ARM FOR A MEDICAL INTERVENTION

CROSS-REFERENCE TO RELATED APPLICATIONS

This application is a National Phase PCT/FR2019/053012, filed on Dec. 11, 2019, which claims priority to French Patent Application No. 1872735, filed on Dec. 12, 2018, the disclosures of which are hereby incorporated by reference in their entireties.

FIELD OF THE INVENTION

The present invention lies within the field of medical robots intended to assist a practitioner in a medical operation. Notably, the invention relates to a medical robot assisted by an electromagnetic navigation system and configured to position an articulated arm of the medical robot in a measurement zone of the electromagnetic navigation system without disturbing, or at least only negligibly disturbing, the measurements performed by the electromagnetic navigation system. The invention relates also to a method for positioning an articulated arm of such a medical robot.

STATE OF THE ART

Many medical operations require a medical instrument (for example a needle, a catheter, an electrode, an ultrasound generator, a drill bit, etc.) to be positioned or displaced very accurately with respect to an anatomical location of interest of a patient. For some operations, there are currently medical robots allowing a practitioner to be assisted in placing, holding or guiding a medical instrument.

Such a medical robot has to be positioned so as to then allow the practitioner to execute an operation plan comprising one or more actions to be performed on an anatomical location of interest of a patient.

Such an operation plan is generally determined by the practitioner, then it is transmitted to the medical robot which stores it in a memory of a control unit incorporated in the medical robot and configured to direct the medical robot.

It is then advisable, in order to position the medical robot optimally to allow the practitioner to execute the actions of the operation plan, to be able to accurately define the position of the anatomical location of interest with respect to the medical robot during the medical operation.

In some systems, and notably in the system described in the U.S. Pat. No. 8774901 B2, the position of the anatomical location of interest of the patient can be defined in a reference frame of the medical robot using an intra-operative image taken during the medical operation. In such a case, the position of the imaging device with respect to the medical robot must be known and fixed. The intra-operative image in fact allows the position of the anatomical location of interest of the patient to be determined with respect to the imaging device. Since the position of the imaging device with respect to the medical robot is fixed and known, it is then possible to determine the position of the anatomical location of interest of the patient with respect to the medical robot.

With such a system, a shift in the position of the anatomical location of interest of the patient during the medical operation will not be able to be detected without another intra-operative image being taken. A shift in the position of the anatomical location of interest may be due, for example, to the movements generated by the breathing of the patient, to the movements of the internal organs, or to the intra-operative manipulations of an operator on the patient.

In such a system, the medical robot is associated with a particular imaging device. The system is generally fixed to the floor of an operating room. The medical robot cannot therefore be used with another imaging device, or even in another operating room without complicated set-up.

Furthermore, such a system requires a determination of an operation plan at the time of the operation, from the intra-operative image. The planning conditions are not therefore optimal for the practitioner who has little time to define the actions to be performed on the anatomical location of interest.

In other systems, and notably in the system described in the patent application US 2016/0157887 A1, the position of the anatomical location of interest of the patient can be defined with respect to the medical robot using an optical navigation system. An optical sensor is placed in proximity to the anatomical location of interest of the patient. Another optical sensor is placed on the medical robot. The optical navigation system allows the position of one sensor to be determined with respect to the other. A medical imaging device is also used to determine the position that a medical tool has to take with respect to the anatomical location of interest within a reference frame of the optical sensor placed at the anatomical location of interest of the patient. The position of the medical tool can then be determined within a reference frame of the medical robot.

Such a system makes it possible to follow any movements of the anatomical location of interest during the operation, notably the movements due to the breathing of the patient or to manipulations of the patient by an operator during the operation.

However, such a system is not suitable for accurately determining the position of an anatomical location of interest situated inside the body of a patient. Indeed, an optical navigation system requires the optical sensors to be visible, with a direct line of sight, to a control device of the optical navigation system.

Also, any object interrupting the line of sight between an optical sensor and the control device of the optical navigation system during the operation would consequently cause errors on the estimation of the position of the medical robot with respect to the anatomical location of interest of the patient, and therefore on the positioning of the medical tool with respect to said anatomical location of interest.

To avoid having to guarantee a direct line of sight between a control device and a sensor of the navigation system, it is possible to envisage replacing the optical navigation system with an electromagnetic navigation system.

The electromagnetic navigation systems do however present the drawback of being sensitive to the interferences and distortions of the electromagnetic field in the presence of metal objects. It is then advisable, for example, for only non-metal materials to enter into the measurement zone of the navigation system. In some cases, aluminum plates are used to isolate a metal part of the medical robot with respect to an electromagnetic field generator of the navigation system.

A motor of an articulation of an articulated arm of a medical robot generally comprises metal parts. Reducing the number of metal parts, or using aluminum plates in the articulated arm of a medical robot consequently reduces the degrees of freedom of the articulated arm. In other words, the number of possible movements of the articulated arm is significantly reduced. It can then become impossible to configure the articulated arm in a position allowing the practitioner to perform certain actions sufficiently accurately on an anatomical location of interest of a patient.

SUMMARY OF THE INVENTION

The aim of the present invention is to remedy all or some of the drawbacks of the prior art, notably those set out hereinabove.

To that end, and according to a first aspect, the present invention proposes a method for positioning an articulated arm of a medical robot to assist a practitioner in a medical operation on an anatomical location of interest of a patient. The medical robot comprises a base to which the articulated arm is linked, and a control unit allowing the articulated arm to be configured in a determined position. The medical robot is assisted by an electromagnetic navigation system comprising an electromagnetic field generator and two electromagnetic sensors. The generated electromagnetic field forms a measurement zone in which the position of a sensor can be determined by the electromagnetic navigation system and communicated to the medical robot. A first sensor is positioned, in a preliminary step, at the anatomical location of interest, a second sensor is positioned on the articulated arm. The method for positioning the articulated arm is noteworthy in that it comprises the following steps:
  a determination, when the two sensors are located in the measurement zone, of a so-called "region of reduced influence", from the position of the electromagnetic field generator and from the position of the sensors,
  a configuration of the articulated arm such that any metal part of the articulated arm located in the measurement zone is situated within the region of reduced influence.

The method for positioning the articulated arm does not include a step of execution of a medical act on the patient. The articulated arm of the medical robot is in fact configured prior to the execution of the medical act by the practitioner.

In the present application, the term "medical" should be considered in the broad sense and can relate equally to a surgical context or a non-surgical context.

"Anatomical location of interest" of the patient is understood to mean at least a part of the human body of the patient for which a treatment is targeted by the medical operation.

In the present application, the term "position" in fact corresponds to the combination of the position and the orientation of an object within a given reference frame which is generally a system of coordinates in three dimensions. The term "pose" is used in the literature to represent this combination of position and orientation of an object in space. The second sensor positioned on the articulated arm of the medical robot is placed at a known position within a reference frame of the medical robot.

The electromagnetic navigation system allows the position of the first sensor and of the second sensor to be determined within a reference frame of the electromagnetic navigation system. Such a reference frame is for example centered with respect to a center of the electromagnetic field generator of said electromagnetic navigation system. The position of the first sensor and the position of the second sensor are therefore known with respect to one another. Since the position of the second sensor is known within a reference frame of the medical robot, the position of the first sensor can be determined within a reference frame of the medical robot. The position of the sensors and the position of the electromagnetic field generator in the reference frame of the navigation system are communicated to the medical robot by the navigation system. The term "position" comprises the position and the orientation in the three spatial dimensions of the reference frame of the navigation system.

The position of the anatomical location of interest of the patient is known with respect to the position of the first sensor. For example, an intra-operative image on which both the anatomical location of interest of the patient and the position of the first sensor appear can be taken during the medical operation.

Knowing the position of the anatomical location of interest with respect to the first sensor and the position of the first sensor with respect to the medical robot, it is possible to determine the position of the anatomical location of interest with respect to the medical robot.

The so-called "region of reduced influence" is a region of the measurement zone in which the introduction of a metal object disturbs the determination of the positions of the first sensor and of the second sensor by the electromagnetic navigation system virtually not at all when said sensors are located in the measurement zone of the electromagnetic field generated by the generator of the electromagnetic navigation system. This region is such that a metal object situated in this region does not create, or only negligibly creates, distortion on a line of the generated electromagnetic field passing through one of the sensors.

It is accepted in the present application that the disturbance on the sensor position measurements induced by the presence of metal parts of the articulated arm 14 of the medical robot 10 in the zone of reduced influence is negligible if the measurement error on the position of a sensor on each axis of a three-dimensional system of coordinates of the reference frame of the navigation system is below a threshold value. This threshold value can, for example, have a value of 1 mm, even 0.5 mm.

As long as the metal parts of the articulated arm of the medical robot remain within this region, it is possible to accurately follow the position of the two sensors, and thus determine the position of the anatomical location of interest with respect to the medical robot.

Such provisions allow the position of the anatomical location of interest of the patient to be determined with respect to the medical robot throughout the duration of the operation, even if metal parts of the robot are located in proximity to the anatomical location of interest, and even if objects block a line of sight between the anatomical location of interest and a control device of the navigation system.

In particular embodiments, the invention can further comprise one or more of the following features, taken alone or according to any technically possible combinations.

In particular embodiments, the electromagnetic field generator takes the form of a plate, and the region of reduced influence is determined as being a region of the measurement zone situated opposite said plate with respect to a plane parallel to the plate and passing through the sensor which is at the greatest distance from the plate in a direction orthogonal to the plate.

In particular embodiments, the region of reduced influence is determined as being a region of the measurement zone which is situated opposite the electromagnetic field generator with respect to a plane orthogonal to a direction passing through a center of the electromagnetic field generator and through the sensor which is at the greatest distance from the center of the electromagnetic field generator.

Such provisions make it possible to ensure that the metal parts of the articulated arm of the medical robot remain "beyond" a plane tangential to a field line passing through said sensor. Said metal parts cannot therefore cut the field lines passing through the sensors, and consequently they disturb the measurements performed by the navigation system virtually not at all.

In particular embodiments, the articulated arm is configured according to an operation plan stored in the control unit of the medical robot. Said operation plan comprises information on at least one action to be performed on the anatomical location of interest of the patient. The configuration of the articulated arm is determined from the positions of the sensors determined by the navigation system to allow the practitioner to perform said action subsequent to the positioning method.

Such provisions make it possible to follow a shift in the position of the anatomical location of interest, that is to say adjust the position of the articulated arm of the medical robot with respect to the position of the anatomical location of interest of the patient, when the anatomical location of interest of the patient undergoes shifts in position due for example to the breathing of the patient, to intra-operative manipulations or to internal movements of the anatomical location of interest. The invention thus allows for an automatic registration of the position of the articulated arm of the medical robot according to movements of the anatomical location of interest of the patient.

In particular embodiments, a tool can be mounted on a tool-holder mounted at a free end of the articulated arm, and an action of the operation plan corresponds to allowing the placement of the tool at a predetermined position, in a predetermined volume or according to a predetermined trajectory, with respect to said anatomical location of interest of the patient.

"Free end" is understood to mean the end of the articulated arm which is not linked to the base of the medical robot.

It should be noted that the medical act as such (for example the insertion of the needle into the anatomical location of interest of the patient) is performed by the practitioner after the method for positioning the articulated arm of the medical robot. The execution of such a medical act does not therefore form part of the method for positioning the articulated arm.

In particular embodiments, a configuration of the articulated arm allowing an action of the operation plan to be performed is determined from:
- a preoperative image comprising information on said planned action to be performed on the anatomical location of interest of the patient,
- an intra-operative image comprising information on the position of the anatomical location of interest of the patient with respect to the position of the first sensor situated at the anatomical location of interest,
- a registration of the intra-operative image with the preoperative image to obtain an image comprising both the information on the planned action to be performed on the anatomical location of interest of the patient and the information on the position of said anatomical location of interest with respect to the position of said first sensor.

The operation plan can in fact be determined by the practitioner during a planning phase based on medical images of scanner, computerized tomography (CT), magnetic resonance imaging (MRI), positron emission tomography (PET), ultrasound, X-ray type, and other such types. The practitioner can then choose a position or a trajectory of the medical instrument with respect to an anatomical location of interest of the patient on one or more medical images.

The real position of the anatomical location of interest of the patient at the time of the operation does not however necessarily correspond to a position predicted or modeled during a preoperative planning phase. It is therefore advantageous to be able to register a preoperative image from which an action to be performed on the anatomical location of interest is planned with an intra-operative image accurately representing the position of the anatomical location of interest of the patient at the time of the operation.

The position of the anatomical location of interest of the patient at the time of the operation can be determined from medical images of scanner, CT, MRI, PET, ultrasound, X-ray, fluoroscopy, cone beam computed tomography (CBCT) type, and other such types.

In particular embodiments, the first sensor comprises elements visible in said intra-operative image, and the geometry of said elements is known.

Such provisions allow the position of the first sensor with respect to the anatomical location of interest to be determined accurately on the intra-operative image.

In particular embodiments, the anatomical location of interest of the patient and the first electromagnetic sensor are situated inside the body of the patient.

With an electromagnetic navigation system, it is not in fact necessary for the sensor positioned at the anatomical location of interest of the patient to be visible.

According to a second aspect, the present invention relates to a medical robot for assisting a practitioner in a medical operation on an anatomical location of interest of a patient. The medical robot comprises a base to which an articulated arm is linked, and a control unit allowing the articulated arm to be configured in a determined position. The medical robot is intended to be assisted by an electromagnetic navigation system comprising an electromagnetic field generator and two electromagnetic sensors. The electromagnetic field generated by said generator forms a measurement zone in which the position of a sensor can be determined by the electromagnetic navigation system and communicated to the medical robot. A first sensor is positioned at the anatomical location of interest, a second sensor is positioned on the articulated arm. The control unit is configured, when the two sensors are located in the measurement zone, to determine a so-called "region of reduced influence" of the measurement zone from the position of the electromagnetic field generator and from the position of the sensors, and to configure the articulated arm such that any metal part of the articulated arm located in the measurement zone is situated within said region of reduced influence.

In particular embodiments, the invention can further comprise one or more of the following features, taken alone or according to any technically possible combinations.

In particular embodiments, the articulated arm comprises a tool-holder at a free end of the articulated arm. The tool-holder is produced in a non-magnetic material and the second sensor is positioned on the tool-holder.

"Non-magnetic material" is understood to mean a material which is not (or is hardly) attracted or repelled by a magnet. For example, the tool-holder is made of plastic, of ceramic, or of series 300 stainless steel.

In particular embodiments, the tool-holder extends in a longitudinal direction of the last section of the articulated arm at the free end of the articulated arm, the tool-holder has a length at least equal to 10 cm, and the second sensor is positioned at a distal end of the tool-holder.

Such provisions allow for an additional margin to ensure that the metal parts of the medical robot are sufficiently far away from the second sensor in order not to disturb, or even only negligibly disturb, the measurement of the position of said sensor by the navigation system.

In particular embodiments, the electromagnetic field generator takes the form of a plate, and the region of reduced influence is determined by the control unit as being a region of the measurement zone situated opposite said plate with respect to a plane parallel to the plate and passing through the sensor which is at the greatest distance from the plate in a direction orthogonal to the plate.

In particular embodiments, the region of reduced influence is determined by the control unit as being a region of the measurement zone which is situated opposite the electromagnetic field generator with respect to a plane orthogonal to a direction passing through a center of the electromagnetic field generator and through the sensor which is at the greatest distance from the center of the electromagnetic field generator.

In particular embodiments, the articulated arm is configured by the control unit according to an operation plan stored in the control unit of the medical robot. Said operation plan comprises information on at least one action to be performed on the anatomical location of interest of the patient. The configuration of the articulated arm is determined from the positions of the sensors determined by the navigation system to allow the practitioner to perform said action subsequent to the positioning method.

In particular embodiments, a configuration of the articulated arm allowing an action of the operation plan to be performed is determined from:
  a preoperative image comprising information on said planned action to be performed on the anatomical location of interest of the patient,
  an intra-operative image comprising information on the position of the anatomical location of interest of the patient with respect to the position of the first sensor situated at the anatomical location of interest,
  a registration of the intra-operative image with the preoperative image to obtain an image comprising both the information on the planned action to be performed on the anatomical location of interest of the patient and the information on the position of said anatomical location of interest with respect to the position of said first sensor.

DESCRIPTION OF THE FIGURES

The invention will be better understood on reading the following description, given as a nonlimiting example, and with reference to FIGS. 1 to 7 which represent.

In these figures, references that are identical from one figure to another designate identical or similar elements. For purposes of clarity, the elements represented are not necessarily to the same scale, unless stipulated otherwise.

DETAILED DESCRIPTION OF AN EMBODIMENT OF THE INVENTION

Figure 1:
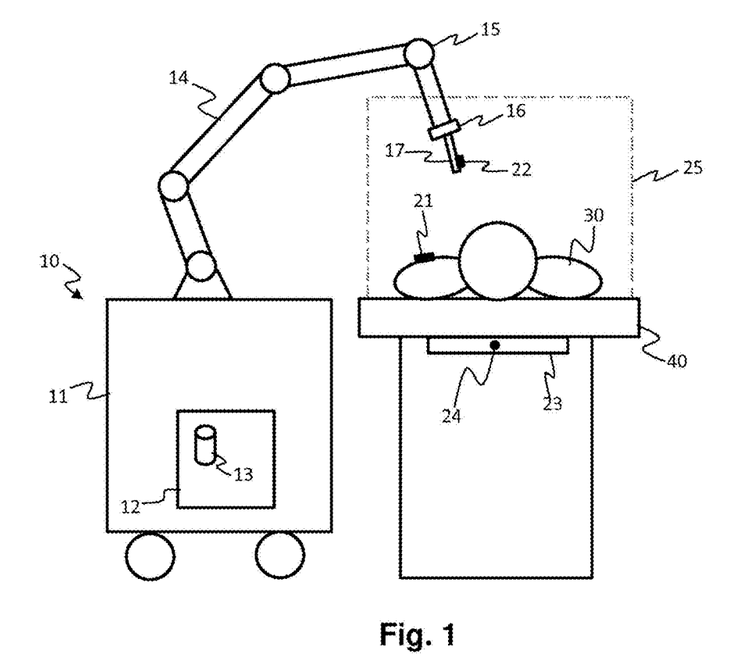
FIG. 1 a schematic representation of a medical robot according to the invention,
  FIG. 2 a schematic representation, seen from above, of the placement of a field generator of an electromagnetic navigation system and of the corresponding measurement zone for a patient stretched out on an operating table,
  FIG. 3 a schematic representation of a so-called "region of reduced influence" of the measurement zone,
  FIG. 4 a schematic representation of the determination of a so-called "region of reduced influence" of the measurement zone for a particular implementation of the invention,
  FIG. 5 a schematic representation of the determination of a so-called "region of reduced influence" of the measurement zone for a particular implementation of the invention,
  FIG. 6 another schematic representation of the particular implementation of the invention described with reference to FIG. 5, FIG. 7 a schematic representation of the main steps of a method for positioning an articulated arm of a medical robot according to the invention.

FIG. 1 schematically represents a medical robot 10 according to the invention, and a patient 30 stretched out on an operation table.

The medical robot 10 comprises a base 11. In the example illustrated in FIG. 1, the base 11 of the medical robot 10 is equipped with wheels, which allow the medical robot 10 to move around in different directions by translational and/or rotational movements. The medical robot 10 comprises an articulated arm 14 of which one end is linked to the base 11. A medical tool can be mounted on a tool-holder 17 at the free end of the articulated arm 14, that is to say at the end of the articulated arm 14 which is not linked to the base 11 of the medical robot 10.

Such a medical robot 10 can then be used to assist a practitioner in positioning, holding or guiding the medical tool. The medical robot 10 then acts as a third hand for the practitioner.

The articulated arm 14 preferably has at least six degrees of freedom to be able to position and/or move the medical tool within a three-dimensional space. Even more preferentially, the articulated arm has 7 degrees of freedom allowing the configuration of the arm to be changed while conserving the position of the tool.

For example, the tool can be a guide for implanting an instrument such as a needle, a catheter, or an electrode in a target zone of an anatomical location of interest of the patient 30.

According to another example, the tool can be a medical instrument, a probe or an electrode that it has to introduce very accurately into a target organ to allow a biopsy, a resection or an ablation of a part of the anatomical location of interest of the patient 30.

Hereinafter in the description, the situation assumed by way of example and in a nonlimiting manner will be the case where a tool-holder 17 is mounted at the free end of the articulated arm 14 of the medical robot 10, and the tool mounted on the tool-holder 17 is a guiding instrument for guiding a needle. As illustrated in FIG. 1, the tool-holder 17 is, for example, mounted on the articulated arm 14 of the medical robot 10 via a flange 16.

It is important for the medical robot 10 to be able to position the tool at a predetermined position, or shift the position of the tool within a predetermined space or according to a predetermined trajectory, with accuracy with respect to the anatomical location of interest of the patient 30.

The articulated arm 14 comprises one or more articulations 15 controlled by a control unit 12 of the medical robot 10. One possible configuration of the articulated arm 14 then corresponds to a set of values of parameters taken by the articulation or articulations 15 of the articulated arm 14 (for example an angle of rotation, a translation distance, etc.).

The control unit 12 comprises, for example, one or more processors and a memory 13 (magnetic hard disk, electronic memory, optical disk, etc.) in which there is stored a computer program product, in the form of a set of program code instructions to be executed to implement the different steps of a method for positioning the articulated arm 14 of the medical robot 10. Alternatively or in addition, the control unit 12 comprises one or more programmable logic circuits (FPGA, PLD, etc.), and/or one or more custom integrated circuits (ASIC), and/or a set of discrete electronic components, etc., suitable for implementing all or part of said steps of said positioning method.

An electromagnetic navigation system is used to allow the position of the anatomical location of interest of the patient 30 to be determined with respect to the medical robot 10. The electromagnetic navigation system comprises an electromagnetic field generator 23 and two electromagnetic sensors 21, 22. A first sensor 21 is placed at the anatomical location of interest 31 of the patient 30. A second sensor 22 is mounted on the articulated arm 14 of the medical robot 10, at a known position within a reference frame of the medical robot 10.

The navigation system can also comprise a centralized control device configured to determine the position of the sensors 21, 22 from measurements performed by said sensors 21, 22. Such a control device is not represented in the figures. It can possibly be incorporated with the electromagnetic field generator 23. The control device is configured to communicate, for example via wireless communication means, the position of the sensors 21, 22 to the control unit 12 of the medical robot 10.

As is known, the electromagnetic sensors 21, 22 comprise, for example, at least two conductive coils which can be configured to measure six degrees of freedom when said sensors 21, 22 are subjected to an external electromagnetic field. Each coil of an electromagnetic sensor 21, 22 produces an induced electrical signal having characteristics which depend on the position of the coil with respect to the electromagnetic field.

The navigation system thus allows the position of the first sensor 21 and the position of the second sensor 22 to be determined within a reference frame of the navigation system when the sensors 21, 22 are located in a measurement zone 25 of the navigation system. Such a reference frame is, for example, centered with respect to a center 24 of the electromagnetic field generator 23.

Figure 2:
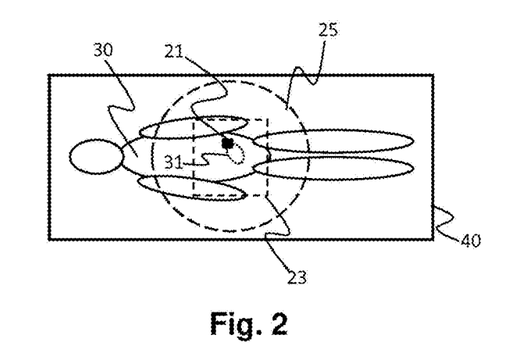

The measurement zone 25 corresponds to a region of the space in which the electromagnetic field emitted by the generator 23 is sufficiently strong to allow the position of an electromagnetic sensor 21, 22 located in this zone to be determined. In the example considered, and as illustrated in FIGS. 1 and 2, the electromagnetic field generator 23 of the navigation system is a plate fixed horizontally under an operating table 40 on which the patient 30 is stretched out. The measurement zone 25 takes the form of a cylinder with a diameter of approximately 500 mm and a height of approximately 600 mm extending above the operating table 40 and whose base is centered on the plate formed by the generator 23. As illustrated in FIG. 2, the electromagnetic field generator 23 is fixed under the operating table 40 at a position such that a sensor 21 placed at the anatomical location of interest 31 of the patient 30 is included in the measurement zone 25.

The electromagnetic navigation system allows the position of the first sensor 21 and the position of the second sensor 22 to be determined in a reference frame of the electromagnetic navigation system. The position of the first sensor 21 and the position of the second sensor 22 are therefore known with respect to one another. Since the position of the second sensor 22 is known in a reference frame of the medical robot 10, the position of the first sensor 21 can be determined in a reference frame of the medical robot 10.

The position of the anatomical location of interest 31 of the patient 30 is known with respect to the position of the first sensor 21. For example, an intra-operative image showing both the anatomical location of interest 31 of the patient 30 and the position of the first sensor 21 can be produced during the medical operation.

To appear in an intra-operative image, the first sensor 21 can, for example, comprise radio-opaque ceramic balls. The geometry of said balls is known in order to be able to accurately determine the position of the first sensor 21 with respect to the anatomical location of interest 31 on the intra-operative image.

Knowing the position of the anatomical location of interest 31 with respect to the first sensor 21 and the position of the first sensor 21 with respect to the medical robot 10, it is possible to determine the position of the anatomical location of interest 31 with respect to the medical robot 10.

Thus, throughout the medical operation, the configuration of the articulated arm 14 of the medical robot 10 can be determined according to the position of the sensors 21, 22 in order to place and hold a medical tool at a predetermined position, shift the position of the tool within a predetermined space and/or according to a predetermined trajectory, accurately, with respect to the anatomical location of interest 31 of the patient 30.

In particular, it is possible to follow the movements of the anatomical location of interest 31 and adjust, or in other words register, the position of the articulated arm 14 of the medical robot 10 according to these movements. Movements of the anatomical location of interest 31 of the patient 30 can be due for example to the breathing of the patient, to intra-operative manipulations on the patient 30, or to movements of internal organs of the patient 30.

In particular implementations, the articulated arm 14 is configured according to an operation plan stored in the control unit 12 of the medical robot 10.

The operation plan comprises information on one or more actions to be performed on the anatomical location of interest 31 of the patient 30. An action of the operation plan corresponds, for example, to being able to manipulate a medical tool in a predetermined space, to placing the tool in a predetermined position, or else to shifting the position of the tool according to a predetermined trajectory with respect to the anatomical location of interest 31 of the patient 30.

The operation plan is created during a planning phase. This planning phase can precede the medical operation, and it is then defined from preoperative medical images. According to another example, the planning phase can be defined during the operation from intra-operative medical images.

During this planning phase, the practitioner defines the different actions which will have to be performed on the anatomical location of interest. The operation plan can, for example, be generated using medical images of CT scan, MRI, PET, ultrasound, X-ray type or other types. An operator, generally the practitioner who will perform the operation using the medical robot 10, selects the parameters of the tool (for example, a length, a diameter, a 3D form, an energy power level to be delivered, a current intensity, a treatment time, etc.). One or more actions can be planned depending on the type of treatment to be performed. The planning can be completely manual, interactive, or completely automated using segmentation and planning algorithms. These decision-assisting algorithms can, for example, be based on expert systems (systems capable of reproducing the cognitive mechanisms of the practitioner by performing reasoning based on facts and known rules) or on intelligent automatic learning mechanisms (for example with convolutional neural networks).

The actions of the operation plan are, for example, encoded in the form of instructions known by the control unit 12 in a computer file. The computer file corresponding to the operation plan can, for example, be generated on a computer that is separate from the medical robot 10. The file is then transmitted to the medical robot 10 and stored in the memory 13 of the control unit 12. This transmission of the computer file can be performed in different ways, conventionally, such as, for example, by a file transmission by USB (Universal Serial Bus) key, or else by a wireless communication. The actions of the operation plan describe, for example, the different positions or the different movements of the tool with respect to the anatomical location of interest 31 of the patient 30. The control unit 12 also knows the geometrical model of the articulated arm 14 and of the tool. For example, the arm 14 is equipped with coders which make it possible to know the angular position of each of its axes and, by calculation, to know the position of the tool. The control unit 12 can then determine, from the information contained in the operation plan, one or more configurations of the articulated arm 14 for which the practitioner will be able to perform the actions provided by the operation plan.

The medical act as such, for example the insertion of the needle into the anatomical location of interest 31 of the patient 30, is only executed by the practitioner after the method for positioning the articulated arm 14 of the medical robot 10. The execution of such a medical act does not therefore form part of the method for positioning the articulated arm 14 according to the invention.

It is advantageous for the practitioner to be able to define the operation plan in a planning phase which precedes the medical operation, for example several days or several hours before the operation. The real position of the anatomical location of interest 31 of the patient 30 at the time of the operation does not however necessarily correspond to a position predicted or modeled during a preoperative planning phase. It is therefore advantageous to be able to register a preoperative image from which an action to be performed on the anatomical location of interest 31 is planned with an intra-operative image accurately representing the position of the anatomical location of interest 31 of the patient 30 at the time of the operation.

Thus, in particular implementations, a configuration of the articulated arm 14 allowing an action of the operation plan to be performed is determined from:
- a preoperative image comprising information on said action,
- an intra-operative image comprising information on the position of the anatomical location of interest 31 of the patient 30 with respect to the position of the first sensor 21 situated at the anatomical location of interest 31,
- a registration of the intra-operative image with the preoperative image to obtain an image comprising both the information on the planned action to be performed on the anatomical location of interest of the patient 30 and the information on the position of said anatomical location of interest 31 with respect to the position of said sensor 21. There are different methods for aligning one image with another. Such methods are considered to be known to the person skilled in the art.

One drawback of the electromagnetic navigation system is that the accuracy of the measurement of a position of a sensor 21, 22 by the navigation system can be disturbed by the presence of a metal object in the measurement zone 25. Notably, the flange 16 on which the tool-holder 17 is mounted and the motorized articulations 15 of the articulated arm 14 of the medical robot 10 generally comprise metal parts. If a metal part intercepts a field line 27 of the electromagnetic field emitted by the generator 23 passing through a sensor 21, 22, it will cause a distortion of the electromagnetic field perceived by said sensor 21, 22. The determination of the position of said sensor 21, 22 by the navigation system will then be falsified.

It is then advisable to ensure that the metal parts of the articulated arm 14 of the medical robot 10 located in the measurement zone 25 do not disturb, or even only negligibly disturb, the measurements of the positions of the sensors 21, 22 by the navigation system.

Figure 3:
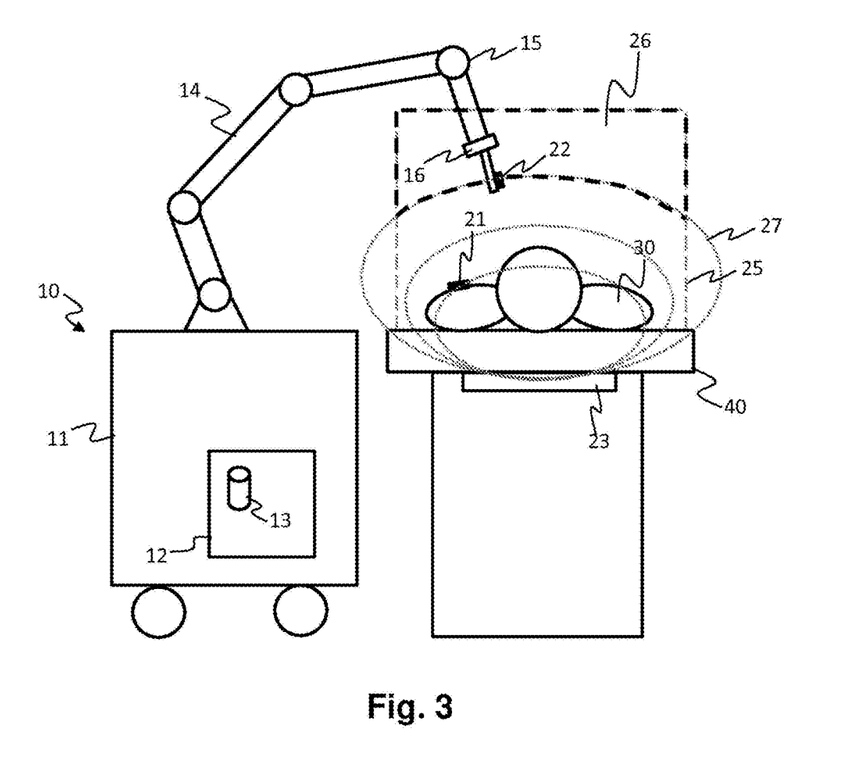

To this end, and as illustrated schematically in FIG. 3, the control unit 12 is configured to determine a so-called "region of reduced influence" 26 of the measurement zone 25 in which the introduction of a metal object disturbs almost not at all the determination of the position of the first sensor 21 and the position of the second sensor 22 by the electromagnetic navigation system when said sensors 21, 22 are located in the measurement zone of the electromagnetic field generated by the electromagnetic field generator 23 of the electromagnetic navigation system. Ideally, the region of reduced influence 26 is defined such that any metal part of the articulated arm 14 of the medical robot 10 located in the measurement zone 25 does not intersect a field line 27 passing through a sensor 21, 22.

The control unit 12 of the medical robot 10 is also designed to configure the articulated arm 14 of the medical robot 10 such that, during the medical operation, any metal part of the articulated arm 14 located in the measurement zone 25 is situated within the region of reduced influence 26.

For an articulated arm 14 of the medical robot 10 that has more degrees of freedom than necessary, several configurations of the articulated arm 14 allowing a planned action to be performed can be envisaged. For example, an anthropomorphic articulated arm 14 with six degrees of freedom can generally position a needle-guide according to a rectilinear direction passing through a predetermined entry point according to several different configurations of its axes. The control unit 12 of the medical robot 10 can then generally choose a configuration of the articulated arm 14 which is compatible with the constraint whereby any metal part of the articulated arm 14 located in the measurement zone 25 must be situated within the region of reduced influence 26.

The region of reduced influence is recalculated as and when the positions of the sensors 21, 22 change, in order to ensure that this constraint is always verified during the operation.

As long as the metal parts of the articulated arm 14 of the medical robot 10 remain within this region of reduced influence 26, it is possible to accurately follow the position of the two sensors 21, 22, and therefore accurately determine the position of the anatomical location of interest 31 with respect to the medical robot 10.

Such provisions allow the position of the anatomical location of interest 31 of the patient 30 to be determined with respect to the medical robot 10 throughout the duration of the operation, even if metal parts of the robot are located relatively close to the anatomical location of interest 31, and even if the anatomical location of interest 31 of the patient 30 undergoes movements during the medical operation.

It is then possible to automatically register the position of the articulated arm 14 of the medical robot 10 according to the movements of the anatomical location of interest 31 during the medical operation.

Figure 4:
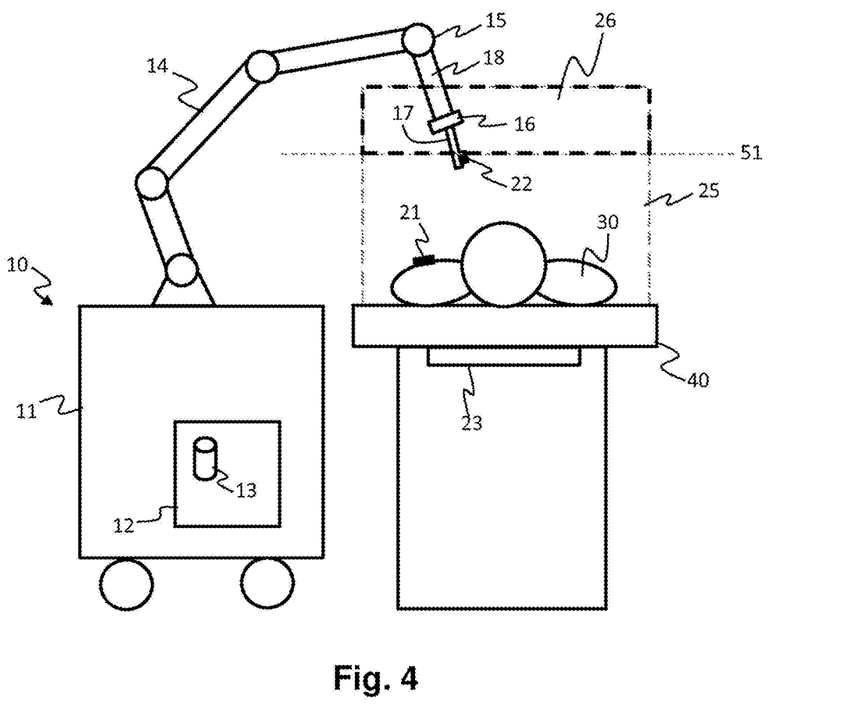

FIG. 4 schematically represents a particular implementation for the determination of the region of reduced influence 26. In this particular implementation, the electromagnetic field generator 23 takes the form of a plate, and the region of reduced influence 26 is the region of the measurement zone 25 situated opposite said plate with respect to a plane 51 parallel to the plate and passing through the sensor 21, 22 which is at the greatest distance from the plate in a direction orthogonal to the plate. In the example illustrated in FIG. 4, the second sensor 22 situated on the articulated arm 14 of the medical robot 10 is the sensor furthest away from the generator 23 in a direction orthogonal to the plate formed by the generator 23. The upper part of the measurement zone 25 delimited by the plane 51 therefore corresponds to the region of reduced influence 26 in which metal parts of the articulated arm 14 can be introduced without significantly disturbing the determination of the position of the sensors 21, 22 by the navigation system.

By thus determining the region of reduced influence 26, the metal parts of the articulated arm 14 remain permanently "above" the sensors 21, 22 with respect to the electromagnetic field generator 23.

The determination of the region of reduced influence 26 according to the particular implementation described with reference to FIG. 4 is simple and particularly well suited when the last section 18 on the side of the free end of the articulated arm 14 has to act on the anatomical location of interest 31 of the patient 30 in a direction substantially vertical with respect to the table 40 and with respect to the generator 23. It is not, however, well suited to the cases where the last section 18 of the articulated arm 14 has to act on the anatomical location of interest 31 of the patient 30 in a direction substantially horizontal with respect to the table 40 and with respect to the generator 23.

Figure 5:
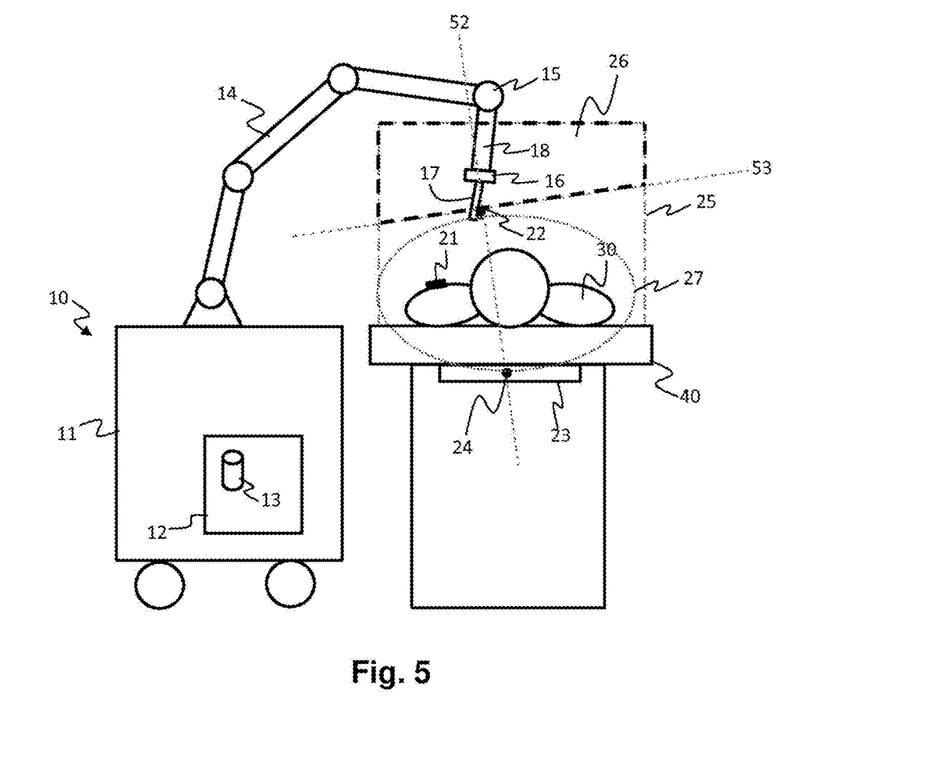

FIG. 5 schematically represents another particular implementation for the determination of the region of reduced influence 26. In this particular implementation, the region of reduced influence 26 is a region of the measurement zone 25 which is situated opposite the electromagnetic field generator 23 with respect to a plane 53 orthogonal to a direction 52 passing through a center 24 of the electromagnetic field generator 23 and through the sensor 21, 22 which is at the greatest distance from the center 24 of the electromagnetic field generator 23.

It should be noted that the position of the center 24 of the electromagnetic field generator 23 and the position of the measurement zone 25 can be determined by the control unit 12 in a reference frame of the medical robot 10 because, on the one hand, the position of the second sensor 22 is known in a reference frame of the medical robot 10 and, on the other hand, the position of the generator 23 can be determined with respect to the position of said second sensor 22 in a reference frame of the navigation system. Transformation matrices can then make it possible, conventionally, to determine the position of the generator 23 in a reference frame of the medical robot 10. The measurement zone 25 is, for its part, known, because it is specified for the navigation system used, with respect to the position of the electromagnetic field generator 23. The specifications of the measurement zone 25 can, for example, be saved in the memory 13 of the control unit 12 of the medical robot 10.

In the example illustrated in FIG. 5, the second sensor 22 situated on the articulated arm 14 of the medical robot 10 is the sensor furthest away from the center 24 of the generator 23. The plane 53 is a plane substantially tangential to a field line 27 passing through the sensor 22. As long as the metal parts of the articulated arm 14 of the medical robot 10 remain "beyond" this plane 53 with respect to the generator 23, they cannot intersect the field lines passing through the sensors 21, 22, and consequently they only negligibly disturb the measurements performed by the navigation system.

It should be noted that, in this particular embodiment, whether the generator 23 has a plate form or else another form is unimportant.

Figure 6:
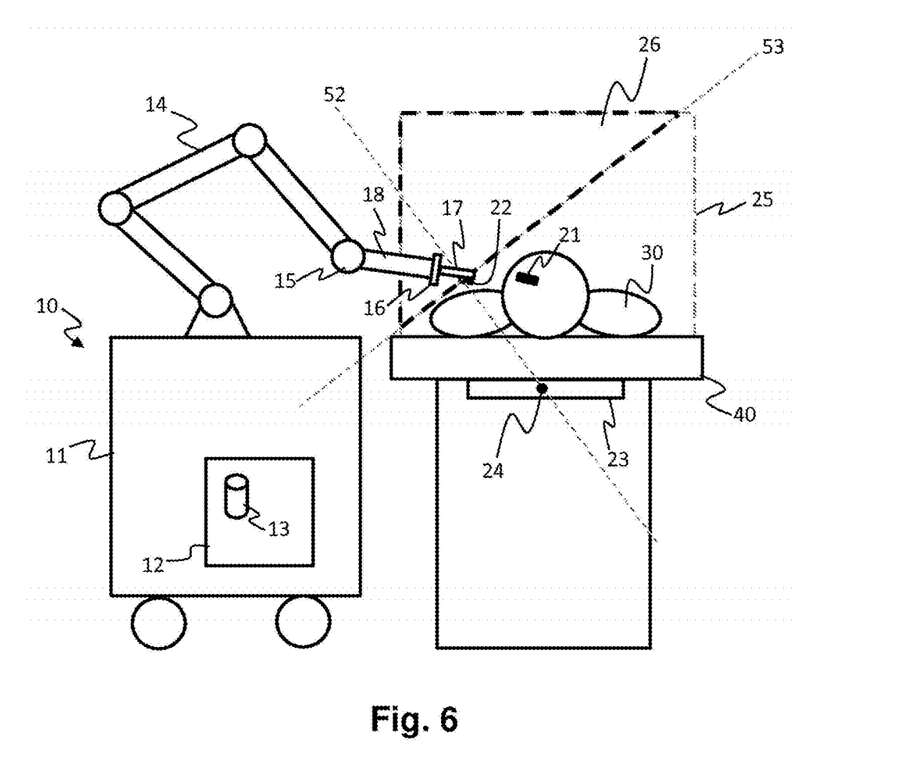

FIG. 6 represents a region of reduced influence 26 determined with the same implementation as that described with reference to FIG. 5 when the last section 18 on the side of the free end of the articulated arm 14 of the medical robot 10 takes a substantially horizontal position.

It appears clearly that this method for determining the region of reduced influence 26 does not prevent such a configuration of the articulated arm 14 of the medical robot 10.

In particular embodiments, the articulated arm 14 comprises a tool-holder 17 at a free end of the articulated arm 14. The tool-holder is produced in a non-magnetic material, that is to say a material which is not (or is hardly) attracted or repelled by a magnet. As nonlimiting examples, the tool-holder can, for example, be made of plastic, of ceramic or of series 300 stainless steel. The second sensor 22, positioned on the articulated arm 14, is positioned on the tool-holder 17.

Preferably, the tool-holder 17 extends in a longitudinal direction of the last section of the articulated arm 14 at the free end of the articulated arm 14, the tool-holder 17 has a length at least equal to 10 cm, and the second sensor 22 is positioned at a distal end of the tool-holder 17.

Such provisions allow for an additional margin to ensure that the metal parts of the medical robot 10 are sufficiently far away from the second sensor 22 so as not to significantly disturb the measurement of the position of said second sensor 22 by the navigation system. Depending on the materials of the medical robot 10 and the type of electromagnetic field generator 23 used, the length of the tool-holder 17 could be different. Notably, it may be advantageous in some cases to have a tool-holder 17 with a length at least equal to 19 cm.

Figure 7:
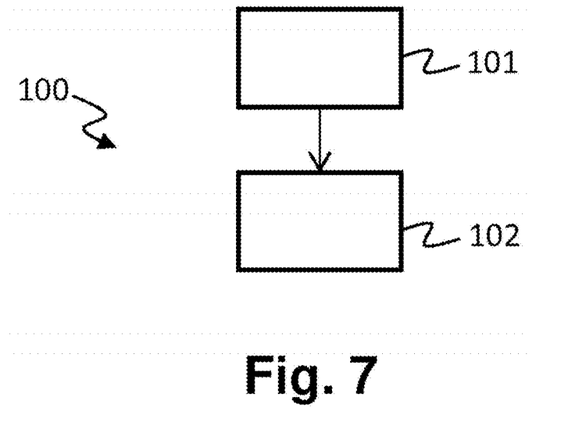

FIG. 7 schematically represents the main steps of a method 100 for positioning an articulated arm 14 of a medical robot 10 as described previously.

Before the execution of the positioning method 100, the first sensor 21 is considered to be positioned at the anatomical location of interest 31 of the patient 30 to be treated. It is also considered that the patient and the electromagnetic field generator 23 are installed with respect to one another such that said first sensor 21 is situated in the measurement zone 25 of the electromagnetic navigation system. Finally, the medical robot 10 is considered to be placed in proximity to the patient 30, at a position allowing the articulated arm 14 of the medical robot 10 to perform all of the actions to be performed on the anatomical location of interest 31.

There are different methods for placing the medical robot 10 at a position at which the articulated arm 14 of the medical robot 10 is capable of performing all of the actions to be performed on the anatomical location of interest 31. It can be a completely manual method, in which an operator moves the medical robot 10 to such a position. It can also be a fully automated method, in which the medical robot 10 comprises, for example, in-space locating means (cameras, range finders, inertial, optical or odometric sensors, etc.) and computation means for detecting such a position and positioning there autonomously.

From that, the method 100 for automatically positioning the articulated arm 14 of the medical robot 10 according to the invention can be implemented to detect and accurately follow the position of the anatomical location of interest 31 during the operation and configure the articulated arm 14 in positions suitable both for allowing the practitioner to carry out the actions to be performed on the anatomical location of interest and to disturb almost not at all the measurements of the electromagnetic navigation system allowing the position of the sensors 21, 22 to be determined.

The method 100 for positioning the articulated arm 14 notably comprises the following steps:
- a determination 101, when the two sensors 21, 22 are located in the measurement zone 25, of a so-called "region of reduced influence" 26 of the measurement zone 25 from the position of the electromagnetic field generator 23 and from the position of the sensors 21, 22,
- a configuration 102 of the articulated arm 14 such that any metal part of the articulated arm 14 located in the measurement zone 25 is situated within the region of reduced influence 26.

The above description clearly illustrates that, through its various characteristics and the advantages thereof, the present invention achieves the objectives set.

In particular, the medical robot 10 can operate in any operating room, it is not linked to a particular operating room, and its position does not have to be known with respect to a particular imaging device. That then limits the costs relating to the robot-assisted medical operations because there is no need to associate a medical robot with each operating room or even to specifically prepare an operating room for a medical robot to be functional therein.

An electromagnetic navigation system is advantageous compared to an optical navigation system because it is not sensitive to any obstacles blocking a direct line of sight between a sensor and a control device of the navigation system.

Also, an electromagnetic navigation system allows the position of a sensor 21 placed inside the human body of a patient 30 to be determined, which makes it possible to treat anatomical locations of interest 31 located inside the body of the patient 30.

By virtue of the electromagnetic navigation system, the medical robot 10 is capable of permanently following the position of the anatomical location of interest 31 of the patient during the operation. The medical robot 10 can therefore adjust the position of its articulated arm 14 according to the movements of the anatomical location of interest 31 during the operation.

The determination of a region of reduced influence 26 according to the position of the sensors 21, 22 throughout the operation allows the control unit 12 of the medical robot 10 to choose configurations of the articulated arm 14 that allow the practitioner to execute the expected actions while ensuring that the measurements supplied by the electromagnetic navigation system are only weakly disturbed by the presence of metal parts in the measurement zone 25 of the navigation system.

More generally, it should be noted that the implementations and embodiments considered above have been described as nonlimiting examples, and other variants can consequently be envisaged.

Notably, different methods have been presented for determining a region of reduced influence 26 of the measurement zone 25. Other methods can, however, be envisaged. Such methods merely correspond to variants of the invention.

The invention claimed is:

1. A method for positioning an articulated arm of a medical robot to assist a practitioner in a medical operation on an anatomical location of interest of a patient, the medical robot comprising a base to which the articulated arm is linked, and a control unit allowing the articulated arm to be configured in a determined position, the medical robot being assisted by an electromagnetic navigation system comprising an electromagnetic field generator and two electromagnetic sensors, the generated electromagnetic field forming a measurement zone in which the position of a sensor can be determined by the electromagnetic navigation system and communicated to the medical robot, a first sensor being positioned, in a step prior to said method at the anatomical location of interest, a second sensor being positioned on the articulated arm, the method comprising:
 - determining, when the two sensors are located in the measurement zone, region of reduced influence of the measurement zone from the position of the electromagnetic field generator and from the position of the sensors, and
 - configuring the articulated arm such that any metal part of the articulated arm located in the measurement zone is situated within the region of reduced influence, wherein said method does not include a step of executing a medical act on the patient.

2. The method of claim 1, wherein the electromagnetic field generator takes the form of a plate, and the region of reduced influence is determined as being a region of the measurement zone situated opposite said plate with respect to a plane parallel to the plate and passing through the sensor which is at the greatest distance from the plate in a direction orthogonal to the plate.

3. The method of claim 1, wherein the region of reduced influence is determined as being a region of the measurement zone which is situated opposite the electromagnetic field generator with respect to a plane orthogonal to a direction passing through a center of the electromagnetic field generator and through the sensor which is at the greatest distance from the center of the electromagnetic field generator.

4. The method of claim 1, wherein the articulated arm is configured according to an operation plan stored in the control unit of the medical robot, said operation plan comprising information on at least one action to be performed on the anatomical location of interest of the patient, the configuration of the articulated arm being determined from the positions of the sensors determined by the navigation system to allow the practitioner to perform said action subsequent to the method for positioning the articulated arm.

5. The method of claim 4, wherein a configuration of the articulated arm allowing an action of the operation plan to be performed is determined from:
 - a preoperative image comprising information on said action,
 - an intra-operative image comprising information on the position of the anatomical location of interest of the patient with respect to the position of the first sensor situated at the anatomical location of interest, and
 - a registration of the intra-operative image with the preoperative image to obtain an image comprising both the information on the planned action to be performed on the anatomical location of interest of the patient and the information on the position of said anatomical location of interest with respect to the position of said first sensor.

6. The method of claim 5, wherein the first sensor comprises elements visible in said intra-operative image, and the geometry of said elements is known.

7. The method of claim 1, wherein the anatomical location of interest of the patient and the first electromagnetic sensor are situated inside the body of the patient.

8. A medical robot for assisting a practitioner in a medical operation on an anatomical location of interest of a patient, the medical robot comprising a base to which an articulated arm is linked, and a control unit allowing the articulated arm to be configured in a determined position, the medical robot being intended to be assisted by an electromagnetic navigation system comprising an electromagnetic field generator and two electromagnetic sensors, the generated electromagnetic field forming a measurement zone in which the position of a sensor can be determined by the electromagnetic navigation system and communicated to the medical robot, a first sensor being positioned at the anatomical location of interest, a second sensor being positioned on the articulated arm, wherein the control unit is configured, when the two sensors are located in the measurement zone, to determine a region of reduce influence of the measurement zone from the position of the electromagnetic field generator and from the position of the sensors, and to configure the articulated arm such that any metal part of the articulated arm located in the measurement zone is situated within said region of reduced influence.

9. The medical robot of claim 8, wherein the articulated arm comprises a tool-holder at a free end of the articulated arm, wherein the tool-holder is produced in a non-magnetic material, and the second sensor is positioned on the tool-holder.

10. The medical robot of claim 9, wherein the tool-holder extends in a longitudinal direction of the last section of the articulated arm at the free end of the articulated arm, the tool-holder has a length at least equal to 10 cm, and the second sensor is positioned at a distal end of the tool-holder.

11. The medical robot of claim 8, wherein the electromagnetic field generator takes the form of a plate, and the region of reduced influence is determined as being a region of the measurement zone situated opposite said plate with respect to a plane parallel to the plate and passing through the sensor which is at the greatest distance from the plate in a direction orthogonal to the plate.

12. The medical robot of claim 8, wherein the region of reduced influence is determined as being a region of the measurement zone which is situated opposite the electromagnetic field generator with respect to a plane orthogonal to a direction passing through a center of the electromagnetic field generator and through the sensor which is at the greatest distance from the center of the electromagnetic field generator.

13. The medical robot of claim 8, wherein the articulated arm is configured according to an operation plan stored in the control unit of the medical robot, said operation plan comprising information on at least one action to be performed on the anatomical location of interest of the patient, the configuration of the articulated arm being determined from the positions of the sensors determined by the navigation system to allow the practitioner to perform said action.

14. The medical robot of claim 13, wherein a configuration of the articulated arm allowing an action of the operation plan to be performed is determined from:
- a preoperative image comprising information on said action,
- an intra-operative image comprising information on the position of the anatomical location of interest of the patient with respect to the position of the first sensor situated at the anatomical location of interest, and
- a registration of the intra-operative image with the preoperative image to obtain an image comprising both the information on the planned action to be performed on the anatomical location of interest of the patient and the information on the position of said anatomical location of interest with respect to the position of said first sensor.

* * * * *